United States Patent [19]

Dory

[11] Patent Number: 4,995,012

[45] Date of Patent: * Feb. 19, 1991

[54] METHOD OF GENERATING AN ELASTIC WAVE

[75] Inventor: Jacques Dory, Coupvray, France

[73] Assignee: EDAP International, France

[ * ] Notice: The portion of the term of this patent subsequent to Aug. 8, 2006 has been disclaimed.

[21] Appl. No.: 390,861

[22] Filed: Aug. 8, 1989

Related U.S. Application Data

[62] Division of Ser. No. 187,178, Apr. 28, 1988, Pat. No. 4,856,107.

[30] Foreign Application Priority Data

Apr. 28, 1987 [FR] France .................. 87 05981

[51] Int. Cl.$^5$ .................. H01R 1/02; A61B 8/00
[52] U.S. Cl. .................. 367/150; 181/175

[58] Field of Search .................. 73/617, 642, 644; 128/24 A, 328, 660, 739, 37–40; 181/113, 119, 123, 280, 283, 176, 206, 175; 367/7, 8, 10, 88, 103, 119, 123, 142, 150, 151, 162, 164, 166, 171, 176; 310/335, 324, 328

[56] References Cited

U.S. PATENT DOCUMENTS 4,856,107 8/1989 Dory .................. 367/150

Primary Examiner—Brian Steinberger
Attorney, Agent, or Firm—William A. Drucker

[57] ABSTRACT

An acoustic filter is provided for attenuating or suppressing the negative pressure half-waves of an elastic wave, comprising an enclosure containing a liquid whose saturating vapor tension is close to the atmospheric pressure. A pump causes the liquid to flow and a regulator fixes its temperature.

2 Claims, 1 Drawing Sheet

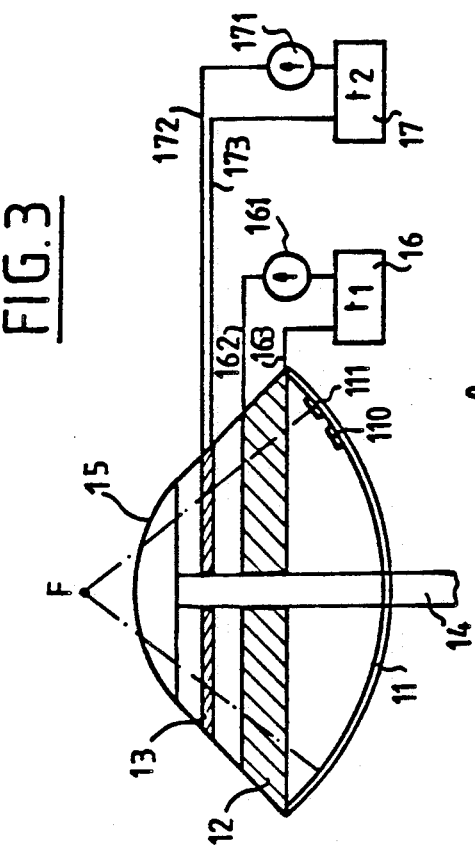
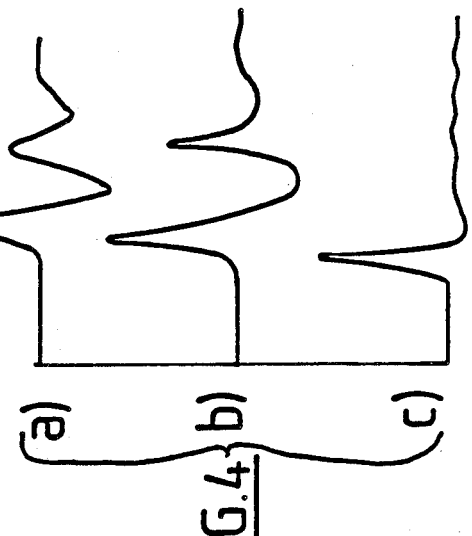
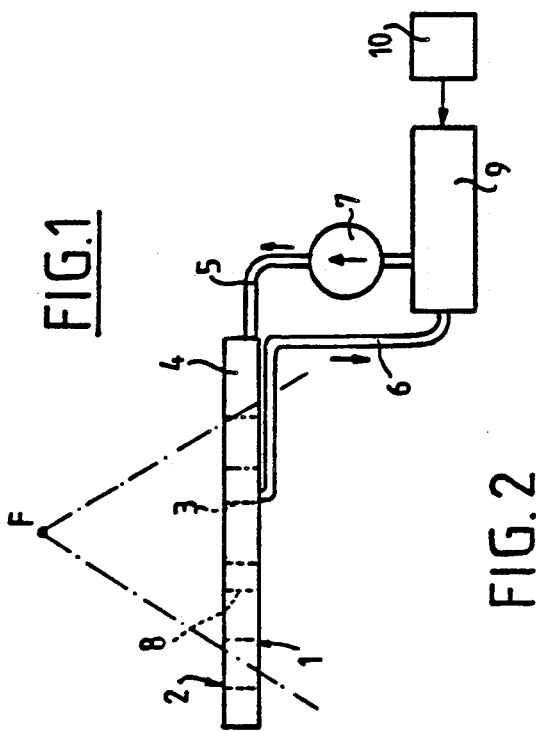
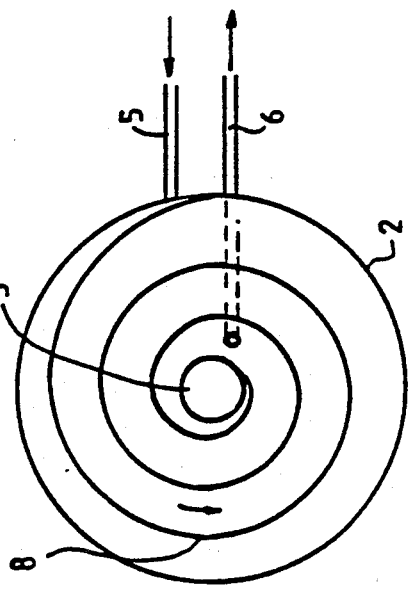

METHOD OF GENERATING AN ELASTIC WAVE

This is a divisional of co-pending application Ser. No. 07/187,178 filed on Apr. 28, 1988 now U.S. Pat. No. 4,856,107.

BACKGROUND OF THE INVENTION

When a high intensity elastic wave generated by an ultra-sonic power focussing radiator, such as that used for example in extra-corporeal lithotripsy, propagates in a liquid medium, the "negative" half-waves of the wave (i.e. corresponding to pressures less than the mean static pressure) may, in the focal region, generate cavitation phenomena with the creation of gas microbubbles, which hinder the propagation of the wave and may also have undesirable effects on the biological tissues through which they pass.

When the wave has the form of a very brief wave train, this phenomenon results in considerable attenuation of the wave which follows the first negative half-wave, and in this case practically only the first positive half-wave is transmitted which, in general, is not the most important one, whence a loss of efficiency. This problem is stated in the French patent application, filed on the same day by the applicant, which offers a first solution for overcoming this drawback.

It is however possible to work with pulses having negative half-waves, knowing that only the first positive half-wave will be usable, and accepting the loss of efficiency which results therefrom. This solution makes it possible to use simplified generators.

But, in this case, considerable additional disturbances may appear, for certain working conditions, which are superimposed on those already mentioned and further reduce the efficiency of the generator.

These disturbances are due to the accumulation of cavitation bubbles which may occur when working at a high rate, in a confined volume. The cavitation bubbles, which cannot be eliminated quickly enough, form a veritable cushion which very rapidly blocks the whole of the acoustic wave. These conditions are present when firing at a gall stone, generally situated and wedged in a volume of very small size. It can be seen in this case that an increase of the firing rate does not reduce the treatment time, which would be logical, but on the contrary reduces its efficiency. It is therefore not possible to use the possibilities of high rate firing offered by present day extra-corporeal lithotripters.

SUMMARY OF THE INVENTION

The invention provides a device for overcoming this drawback and makes high rate firing possible without loss of efficiency, which must lead to extremely reduced treatment times.

The applicant has discovered, during experiments carried out "in vitro", in large sized tanks, that it was possible, under certain experimental conditions, to increase the firing rate up to about 100 Hz, before an appreciable lowering of efficiency occurs. This has made it possible under these conditions to fragmentize gall stones in a minute, whereas the same operation, carried out "in vivo", and at the more reduced rate tolerable by the patient, may exceed 45 minutes.

The applicant has interpreted this fact by considering that one of the causes is that, in a non confined medium, the cavitation bubbles are more readily removed than in a confined medium, and thus disappear between two successive firings.

It has been discovered that after passing through the focal zone the wave, on the assumption that it is not absorbed by a gall stone, has only a single positive half-wave. The applicant explains this fact by considering that the energy of the negative half-waves was absorbed by the formation of the vapor bubbles.

He concludes therefrom, that under these particular experimental conditions not possible "in vivo" the vapor bubbles which are formed on passage of the wave only exist for a very short time, of the order of 1/100th second.

Starting from this discovery, the invention aims at producing such a type of wave for pressures substantially less than that prevailing at the level of the focal center, preferably upstream thereof, in a zone situated outside the patient, where the energy is not yet very concentrated, and it consists in using for this an acoustic filter having a non linear transmission characteristic in amplitude as a function of the pressure of the wave.

According to a feature of the invention, such a filter will be very simply constructed using a liquid for transmitting the ultra-sounds whose vapor tension is very close to the atmospheric pressure and in which, consequently, cavitation may appear for relatively low ultrasonic pressures. It is in fact known that cavitation may occur when the instantaneous "negative" pressure becomes, in absolute value, equal to or greater than the difference between the vapor pressure and the mean static pressure, close in this case to the atmospheric pressure.

In a preferred embodiment, such a filter is formed by causing the low vapor tension transmission liquid to flow between two parallel plates made from a material transparent to the elastic waves, for example a plastic material such as polymethylpentene.

To avoid accumulation of the cavitation bubbles in the space between the plates, rapid flow of liquid is provided so that the bubbles are rapidly removed as they are formed.

In such a device, the vapor tension of the transmission liquid is a critical parameter. Since this parameter varies with the temperature, according to one feature of the invention, this latter is measured and regulated. The control of the temperature offers the great advantage of making it possible to adjust the vapor tension to an optimum value, and to have very efficient and very stable filtering.

The passage through the filter may also have a favorable action on the form of the wave produced. In fact, the speed of sound through a liquid varies as a function of the pressure and increases therewith, this phenomenon also depending on the temperature. The result is that, when a wave of considerable amplitude passes through a liquid medium, the positive fronts tend to steepen, since the positive peaks tend to catch up with the beginning of the pulse. The reverse phenomenon occurs for the negative fronts, which tend to spread out.

Using a relatively thick acoustic filter, it will then be possible, by controlling the temperature, to control the form of the signal and to optimize it.

According to another feature of the invention, two filters will be disposed in cascade, the first one, relatively thick, serves for improving the form of the signal using the speed non linearity mentioned above, the second, thinner, using the amplitude non linearity related to cavitation for eliminating the negative components.

BRIEF DESCRIPTION OF THE DRAWINGS

The invention will be better understood from the following description.

In the accompanying drawings:

FIG. 1 shows schematically an acoustic filter, non linear in amplitude, in accordance with a preferred embodiment of the invention; of which FIG. 2 shows, in a top view, the cavity in which the liquid flows;

FIG. 3 shows schematically an ultrasonic power radiator equipped with such a filter and a filter which is non linear in speed; and FIG. 4 illustrates the waveforms at the input and the output of the two filters.

DESCRIPTION OF THE PREFERRED EMBODIMENT

In FIGS. 1 and 2 a filter has been shown, non linear in amplitude, for use with an extra-corporeal lithotriptor of the type described in French patent No. 83 200 41 filed on the Dec. 14, 1983, in the name of the applicant, for "Ultrasonic pulse apparatus for destroying gall stones".

This filter is formed by an annular cavity formed in a disk closed by two plates 1 and 2 made from a plastic material transparent to the elastic waves. A circular orifice 3 is formed in the center of the disk for passing an echographic locating probe, not shown in the drawings. The filter is traversed by the beam of elastic waves, focussed at F, generated by a radiator not shown. A low vapor tension liquid 4 which, by way of example, will be a freon having a boiling point between 40° and 45° C., is introduced into the cavity through a duct 5 and leaves through a duct 6, its flow being ensured by a pump 7. The flow speed is for example between 10 cm and 1 m/s.

A spiral dividing wall 8 is mounted inside the annular cavity for providing homogeneous distribution of the liquid flow and thus the immediate elimination of any gas bubble. This arrangement is given by way of example and other forms may be envisaged for the dividing wall; it is also possible to provide several liquid inlets and outlets, or else annular shaped inlets and outlets, so as to remove the parasite bubbles more rapidly.

The thickness of the disk is not critical. It may for example be equal to 1 cm. A small thickness facilitates the rapid flow of the liquid.

In its flow path, the liquid passes through a receptacle 9 equipped with a temperature regulation device controlled by a regulation circuit 10 which keeps the temperature at a given value, so as to obtain the desired vapor tension. By way of example, the temperature will be regulated to a value between 25° and 40° C.

Under these conditions, each acoustic pulse having negative half-waves causes cavitation which absorbs the energy of said half-waves. The microbubble thus generated is eliminated by flow of the liquid before the next pulse arrives half-waves thereof.

FIG. 3 shows a treatment head used in lithotripsy. It is formed by a spherical cup 11 lined with piezo-electric transducer elements as described in the above French patent. Only two elements 110, 111 have been shown so as to simplify the drawing. Two filters 12 and 13 are placed in the path of the elastic wave beam generated by the transducer elements, when they are excited for example in the way described in said patent, and focussed at F. The filter 12 is non linear in speed and its thickness is of the order of 5 cm. Filter 13 is non linear in amplitude and its thickness is of the order of 1 cm. An echographic location probe 14 is placed in the center of the cup. The assembly is placed in a pocket filled with water and closed by a flexible membrane 15.

Thermostat controlled tanks 16 and 17 regulate the temperatures of the water of the pocket and of the liquids contained in both filters.

Each of the two filters has the structure shown in FIGS. 1 and 2.

In filter 13, a liquid is caused to flow having a low vapor tension at the reference temperature $t_2$ of the regulation, such as a freon, so as to obtain non linearity in amplitude in algebraic value, i.e. absorption of the energy of the negative half-waves.

On the other hand, in filter 12, a liquid is caused to flow which may be water, not subjected to cavitation at the reference temperature $t_1$ of the regulation, which may be close to the ambient temperature. The flow of this liquid is simply intended to homogenize the temperature, on which the speed non linearity effect depends.

The flow of the liquid through filter 12 is caused by pump 161, 162 being the inlet duct for the liquid and 163 the outlet duct.

Similarly, the flow of liquid through filter 13 is provided by a pump 171, 172 being the inlet duct for the liquid and 173 the outlet duct.

Since the filters described play acoustically the role of plates with parallel faces, they only introduce a negligible shift of the focal center of the device. In any case, the modification of the focal center introduced by the filters may be corrected if necessary. With the filters located upstream of the focal region (in the embodiment described, they are placed more precisely inside pocket 15 which contains the coupling liquid), the focal region remains directly usable for treatment. The filters could be placed downstream of the focal center F of the radiator, but it would then be necessary to refocus the downstream ultrasonic beam by means of an acoustic lens.

In FIG. 4, at (a), the waveform has been shown of an acoustic pulse generated by a transducer such as the one described in the above French patent No. 83 200 41; at (b) the waveform of this pulse after passing through filter 12 and at (c) the waveform obtained after passing through the filter 13. It can be seen that passage through the speed non linear filter simply results in steepening the fronts of the negative half-waves what is called a "unfurling" of the wave, whereas passage through the amplitude non linear filter suppresses practically completely the negative half-waves.

The method of the invention may be combined with that which is described in the above French patent application, filed on the same day. In fact, according to this application, the waveform of the pulse generated by the power radiator has undergone at least partially suppression of the negative half-waves. If this suppression is imperfect, it may be completed by means of an amplitude non linear filter of the above described type.

It should be understood that the amplitude non linear filter of the invention may be associated with any type of ultrasonic power transducer, for attenuating or suppressing the undesirable negative half-waves of the wave which it generates.

The saturating vapor tension of the liquid of said filter at the reference temperature may deviate all the more from the mean static pressure which prevails there the higher the power of the negative half-waves of the wave which passes through it, the amplitude non linearity being related to the formation of cavities filled with vapor within the liquid.

What is claimed is:

1. A method of generating an elastic wave comprising the steps of:
   (a) generating an elastic wave having positive and negative pressure half waves focused at a focal region;
   (b) interposing an acoustic filter in the path of said wave upstream of said focal region to attenuate the negative pressure half waves of said elastic wave, said path including a liquid therein having a predetermined temperature and mean static pressure when said elastic wave is transmitted therethrough in which the vapor tension of said liquid at said temperature, is selected at a predetermined value for causing vapor filled cavities to be formed within said liquid; and
   (c) transmitting said elastic wave through said acoustic filter to attenuate the negative pressure half waves of said elastic wave.

2. The method of claim 1 further including the step of placing said acoustic filter perpendicular to the axis of said elastic wave and providing said filter with a central opening for the passage of an auxiliary echographic beam.

* * * * *